United States Patent [19]

Smith

[11] 4,005,113

[45] Jan. 25, 1977

[54] MULTI-STEP PROCESS FOR PREPARATION OF TETRAHYDROFURAN STARTING FROM PROPYLENE, OXYGEN AND A CARBOXYLIC ACID

[75] Inventor: William E. Smith, Schenectady, N.Y.

[73] Assignee: General Electric Company, Pittsfield, Mass.

[22] Filed: May 27, 1975

[21] Appl. No.: 581,266

Related U.S. Application Data

[62] Division of Ser. No. 420,853, Dec. 3, 1973, abandoned.

[52] U.S. Cl. .......................... 260/346.1 R; 260/491
[51] Int. Cl.² ........................................ C07D 307/08
[58] Field of Search ............ 260/346.1 R, 491, 468

[56] References Cited

UNITED STATES PATENTS

| | | | |
|---|---|---|---|
| 3,007,973 | 11/1961 | Weisemann | 260/638 HF |
| 3,014,970 | 12/1961 | Johnson et al. | 260/638 HF |
| 3,022,340 | 2/1962 | Bloch | 260/491 |
| 3,119,876 | 1/1964 | Jaros et al. | 260/638 HF |
| 3,231,621 | 1/1966 | Slaugh | 260/491 |
| 3,239,566 | 3/1966 | Slaugh et al. | 260/491 |
| 3,239,569 | 3/1966 | Slaugh et al. | 260/491 |
| 3,378,590 | 4/1968 | Usami | 260/632 HF |
| 3,420,898 | 1/1969 | Winkle et al. | 260/491 |
| 3,546,278 | 12/1970 | Hayden et al. | 260/497 A |
| 3,578,698 | 5/1971 | Hayden | 260/491 |
| 3,670,014 | 6/1972 | Fernholz | 260/497 A |

FOREIGN PATENTS OR APPLICATIONS

| | | | |
|---|---|---|---|
| 1,170,222 | 11/1969 | United Kingdom | 260/346.1 |

OTHER PUBLICATIONS

Adkins et al., J. Am. Chem. Soc., vol. 71, p. 3051–3055 (1949).
Hatch, Higher Oxo Alcohols, pp. 2, 3, 13, 20–23 (1959).

*Primary Examiner*—Natalie Trousof
*Assistant Examiner*—Bernard Dentz
*Attorney, Agent, or Firm*—Donald M. Papuga; William F. Mufatti

[57] ABSTRACT

A process for preparing tetrahydrofuran the last step of which comprises heating a carboxylic acid of 1,4-butanediol with water in the presence of a hydrolysis-dehydroacyloxylation catalyst.

2 Claims, No Drawings

MULTI-STEP PROCESS FOR PREPARATION OF TETRAHYDROFURAN STARTING FROM PROPYLENE, OXYGEN AND A CARBOXYLIC ACID

This is a division of application Ser. No. 420,853, filed Dec. 3, 1973, now abandoned.

This invention relates to a process of preparing tetrahydrofuran which comprises heating a carboxylic acid diester of 1,4-butanediol with water in the presence of a hydrolysis-dehydroacyloxylation catalyst.

BACKGROUND OF THE INVENTION

It is known in the art that tetrahydrofuran may be made by a number of different methods; the more prominent methods are by the catalytic hydrogenation of furan or by the dehydration of 1,4-butanediol.

In practice, the tetrahydrofuran is most often produced by a series of reactions starting with the reaction of formaldehyde and acetylene in the presence of a cuprous acetylide complex to form butynediol. Butynediol is converted on hydrogenation to butanediol. The 1,4-butanediol is converted to tetrahydrofuran as indicated above.

Additionally, tetrahydrofuran is prepared from maleic acid, its esters, maleic anhydride, fumaric acid, its esters, succinic acid, its esters, succinic anhydride, γ-butyrolactone, or mixtures of these compounds by hydrogenation over a hydrogenation catalyst.

However, these methods involve considerably expensive equipment and the handling of hazardous materials. Also, catalysts, in some cases may be expensive, and in other instances may be easily poisoned.

Tetrahydrofuran is a useful solvent for natural and synthetic resins, particularly vinyls. Also, it is used as an intermediate in the manufacture of nylon, 1,4-dichlorobutane and polyurethanes.

DESCRIPTION OF THE INVENTION

It has been discovered that tetrahydrofuran may be inexpensively prepared from a carboxylic acid diester of 1,4-butanediol by heating it with water in the presence of a heterogeneous hydrolysis-dehydroacyloxylation catalyst. By this method, tetrahydrofuran is produced in essentially quantitative yields. Also, the hydrolysis-dehydroacyloxylation catalyst of the instant invention is stationary and permanent and therefore may be continually reused.

Another object of this invention is to produce tetrahydrofuran from inexpensive starting materials, i.e., propylene, carbon monoxide, hydrogen and oxygen, by way of several intermediate steps.

The hydrolysis-dehydroacyloxylation catalysts which may be employed in the practice of this invention are those which promote hydrolysis, evolution of the carboxylic acid and ring closure. In the case of the diacetate ester, the catalyst is a hydrolysis-dehydroacetoxylation catalyst. Suitable hydrolysis-dehydroacyloxylation catalysts include zeolites, silica, alumina, silica-aluminas, silica-magnesias, acidic clays, and the like.

The zeolite hydrolysis-dehydroacyloxylation catalysts which may be used in the instant invention include the synthetic and natural zeolites, also known as molecular sieves. These zeolites are well known in the art and are detailed in *Molecular Sieves*, Charles K. Hersh, Reinhold Publishing Company, New York (1961) which is incorporated herein by reference. Representative nautral zeolites which may be employed in the instant invention include those in Table 3–1 on page 21 of the Hersh reference while representative molecular sieves include those in Table 5–1 on page 54 of the Hersh reference. Additional zeolite catalysts are set forth in *Organic Catalysis Over Crystalline Aluminosilicates*, P. B. Venuto and P. S. Landis, Advances in Catalysts, Vol. 18, pp. 259 to 371 (1968), incorporated herein by reference.

The silica-alumina hydrolysis-dehydroacyloxylation catalysts which may be used vary in composition from pure silica to pure alumina whereas the silica-magnesias vary in composition from pure silica to predominantly magnesia.

The acidic clay hydrolysis-dehydroacyloxylation catalysts which may be used in the instant invention include clays containing the minerals kaolinite, halloysite, montmorillonite, illite, quartz, calcite, liminomite, gypsum, muscavite and the like, either in naturally acidic forms or after treatment with acid.

The catalyst is preferably used in the form of a bed through which the reactants are passed.

The carboxylic acid diesters of 1,4-butanediol which are suitable in the instant invention preferably contain 2 to 8 carbon atoms. A preferred carboxylic acid diester of 1,4-butanediol is the diacetate of 1,4-butanediol.

The amount of water used is only that necessary to cause the reaction to proceed to a satisfactory extent. In absence of added water, the conversion of the diacetate to tetrahydrofuran does not proceed and it is passed through the tube essentially unchanged. Generally, we have found that the water and diacetate may be present in proportions varying from about 1 part water to about 10 parts diacetate, to about 10 parts water to 1 part diacetate. As the amount of water used increases, this adds to the volume of the reaction product from which the tetrahydrofuran must be isolated. Accordingly, one should employ only the minimum amount of water needed to cause the reaction to go at optimum rates and yields. Preferably, the water employed in the instant invention is in the form of steam.

The temperature at which the process can be carried out varies widely. Temperatures ranging from about 125° to about 300° C. are generally adequate although higher temperatures can be used. Preferably, the reaction is carried out at a temperature of from about 180° to about 270° C. The maximum depends upon destruction of the product, olefin formation occurring under too rigorous conditions.

Although only atmospheric pressure is normally required, it will be of course apparent to those skilled in the art that superatmospheric pressure or subatmospheric pressure may be used where conditions and concentrations so dictate.

The process may be illustrated, taking the diacetate of 1,4-butanediol as an example, by the following equation:

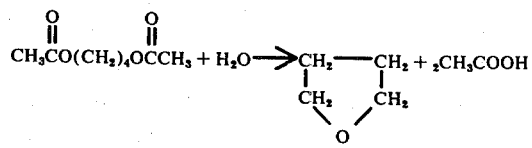

The above transformation is actually the net result of two consecutive reactions represented by the following equations:

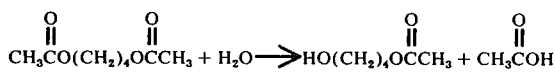

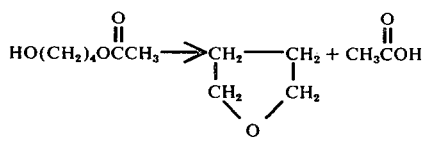

In copending application A, Ser. No. 365,228 of William E. Smith filed May 30, 1973 and assigned to the same assignee as the present invention and now abandoned, there is disclosed and claimed a process for making butanediols by reacting propylene, oxygen and acid to produce an allyl carboxylate which is then hydroformylated to produce the mixture of the corresponding aldehydes. Hydrogenation of the mixture produces a mixture of the esters of the corresponding diols. In copending application B. Ser. No. 365,231 of William E. Smith filed May 30, 1973 and assigned to the same assignee as the present invention and now abandoned, there is disclosed and claimed a process wherein the hydrogenation is accomplished during the hydroformylation reaction. De-esterification of the diol ester mixture produces the desired butanediols which can be separated by distillation. These copending applications A and B are incorporated herein by reference.

In carrying out the preparation of tetrahydrofuran starting from propylene, oxygen and a carboxylic acid, the procedures disclosed in copending applications A and B may be used to obtain the carboxylic acid esters of 1,4-butanediol. These involve (a) reacting propylene, oxygen and a carboxylic acid to form the corresponding allyl carboxylate; (b) converting the allyl carboxylate under hydroformylation-hydrogenation conditions to a mixture comprising the carboxylic acid esters of 1,4-butanediol, 1,2-butanediol and 2-methyl-1,3-propanediol; (c) heating the diol esters with water in the presence of a hydrolysis-dehydroacyloxylation catalyst to form the tetrahydrofuran and the carboxylic acid; and (d) isolating the carboxylic acid in a form suitable for recycling to (a).

To varying extents depending on reaction conditions 1,4-butanediol diacetate is formed in this sequence, either by disproportionation of the monoacetate (which affords the diacetate and diol) or by esterification of the monoacetate with acetic acid present as a decomposition product.

Specifically, this overall process for preparing tetrahydrofuran comprises (a) reacting propylene, oxygen, and a carboxylic acid in the presence of a catalyst comprising a Group VIII noble metal, or its salts, or its oxides or mixtures thereof at a temperature sufficiently high to provide the desired rate of formation of the corresponding allyl carboxylate but below the temperature at which substantial degradation of the allyl carboxylate occurs; (b) converting the alkyl carboxylate under hydroformylation-hydrogenation conditions to a mixture comprising the carboxylic acid esters of 1,4-butanediol, 1,2-butanediol and 2-methyl-1,3-propanediol; (c) heating said mixture with water in the presence of a hydrolysis-dehydroacyloxylation catalyst to convert the 1,4-butanediol diester present, as well as the monoester and diol, to tetrahydrofuran and the carboxylic acid; and (d) isolating the carboxylic acid in a form suitable for recycling to (a).

More specifically, the process of producing tetrahydrofuran comprises (a) reacting propylene, oxygen and acetic acid in the presence of a catalyst comprising a Group VIII noble metal, or its salts or its oxides or mixtures thereof, at a temperature sufficiently high to provide the desired rate of formation of allyl acetate but below the temperature at which substantial degradation of allyl acetate occurs; (b) converting the allyl acetate under hydrogenation-hydroformylation conditions to a mixture comprising a significant amount of 1,4-butanediol diacetate in addition to the monoacetate and diol and the corresponding derivatives of 2-methyl-1,3-propanediol and 1,2-butanediol; (c) heating said mixture with water in the presence of a hydrolysis-dehydroacyloxyation catalyst to convert the diacetate of 1,4-butanediol present as well as the monoacetate and diol to tetrahydrofuran and acetic acid; (d) isolating the acetic acid in a form suitable for recycling to (a).

The conditions under which the carboxylic acid esters of 1,4-butanediol, 1,2-butanediol and 2-methyl-1,3-propanediol are formed from propylene, oxygen and acids by way of an intermediate step are disclosed in copending applications A and B discussed above and incorporated herein by reference.

The hydrolysis-dehydroacyloxylation mixture can be passed over the catalyst in the liquid phase, vapor phase or liquid-vapor phase. Preferably, it is used in the vapor phase.

For most instances, the reaction is carried out by passing the carboxylic acid esters of 1,4-butanediol and water through a heated catalyst bed. Thereafter, the product is distilled to effect isolation of acetic acid and an azeotrope containing tetrahydrofuran and water. Well-known techniques of purification of the fractions can be used to obtain the maximum yield of tetrahydrofuran.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

Apparatus —A vertical hot tube reactor (16 mm ID × 70 cm effective length) is constructed from heavy wall glass, with 24/40 male and female joints. Vigreaux points are indented just above the male joint to support catalyst pellets. Thermocouple leads are fastened into three other Vigreaux indentations at points along the length. Three 4 ft. × 1 inch Briskheat glass insulated heating tapes are wound onto the tube, covered wih glass wool and glass tape, and connected to separate variable transformers. The tube exit is connected by a gooseneck (also heated) to an efficient condenser and collection vessel. A three necked flask serves as the evaporator, with the reactants added from addition funnels in side necks. Nitrogen carrier gas is passed through to provide residence times on the order of 3 to 10 seconds. EXAMPLE 1

The tube reactor described above is charged with 89 grams of silica-alumina catalyst (87% silica —13% alumina, 3/16 × 3/16 pills, Davison Chemical Grade 970) and is maintained at 220°–250° C while 50.0 grams of 1,4-butanediol diacetate and 50 ml. of water, admitted to the evaporator simultaneously from separate addition funnels, are copassed through over a one hour period. Quantitative glpc analysis (propionic acid internal standard) of the effluent shows the presence of 9.0 grams of 1,4-butanediol diacetate (18% recovery), 16.3 grams of tetrahydrofuran (96% yield based on 82% conversion), and 28.2 grams of acetic acid (100% yield based on 82% conversion). No butanediol or butanediol monoacetate is detected.

On distillation, the tetrahydrofuran-water azeotrope is easily separated, leaving a water-acetic acid-butanediol diacetate residue which can be further distilled to afford materials for recycle.

EXAMPLE 2

The tube reactor is charged with 85 grams of silica-magnesia catalyst (70% silica- 30% magnesia, 3/16 × 3/16 pills, Davison Chemical) and maintained at 220°–250° C. As in Example 1, 50.0 grams of 1,4-butanediol diacetate and 50 ml. of water are copassed over one hour. The effluent contains, as shown by quantitative glpc analysis, 12.2 grams of the unconverted butanediol diacetate (24% recovery), 15.1 grams of tetrahydrofuran and 24.4 grams of acetic acid (96% and 93% yields, respectively, based on 76% conversion), and 0.1 grams of 4-acetoxybutanol (0.3% yield).

EXAMPLE 3

The tube reactor, charged with 110 grams of alumina catalyst (⅛ pellets, Harshaw Al-0104T), is maintained at 250° C while 25.0 grams of 1,4-butanediol diacetate and 50 ml. of water are admitted to the evaporator simultaneously from different addition funnels over a 20 minute period. The aqueous effluent collected contains tetrahydrofuran, acetic acid, and about 10% of the original diacetate. The mixture is again taken through the tube. The effluent from this second pass contains, as found by quantitative glpc analysis, 0.3 grams of residual butanediol diacetate (1% unconverted), 9.2 grams of tetrahydrofuran (90% yield), and 15.9 grams of acetic acid (93% yield).

EXAMPLE 4

A 50.0 gram mixture containing 31.7 grams of 4-acetoxybutanol, 10.2 grams of 1,4-butanediol diacetate, a very small amount of 1,4-butanediol, and oxo by-products, (about 6 grams of acetate derivatives of 2-methyl-1,3-propanediol and 1,2-butanediol) is copassed with 50 ml. of water through the tube reactor and alumina catalyst described in Example 3, at 250°–270° C. over a one-hour period. A glpc analysis of the effluent shows the presence of tetrahydrofuran, acetic acid and a few other minor components, but no 1,4-butanediol derivatives. The product mixture is distilled through a 300 mm. Vigreaux column. The first 54 grams taken off (boiling over the 64°–100° C. range) contains, as shown by quantitative glpc analysis, all of the tetrahydrofuran formed — 20.4 grams, corresponding to a 95% yield based on conversion of all 1,4-butanediol monoacetate and diacetate initially present. Analysis of the total distillate shows the presence of 24.3 grams of acetic acid.

EXAMPLE 5

The tube reactor is charged with 88.1 grams of Linde 13X zeolite (150 pellets, pretreated at 200° C. with a tetrahydrofuran-acetic acid vapor mixture) and maintained at 190°–230° C. while 50.0 grams of 1,4-butanediol diacetate and 60 ml. of water are copassed, as in Examples 1–3, over a 1 hour period. The effluent is recycled three times until the diacetate is essentially converted. Quantitative glpc analysis of the final effluent shows the presence of 0.4 grams of butanediol diacetate (1% recovery), 9.5 grams of tetrahydrofuran (47% yield) and 30.4 grams of acetic acid (89% yield). A considerable amount of low boiling material is produced using this method.

EXAMPLE 6

A mixture of completely acetylated oxo acetates composed of 37.8 grams of 1,4-butanediol diacetate, 4.7 grams of 2-methyl-1,3-propanediol diacetate and 7.5 grams of 1,2-butanediol diacetate is copassed with 50 ml. of water through the tube and the silica-alumina catalyst described in Example 1, at 220°–250° C., over a 1 hour period. Quantitative glpc analysis of the effluent indicates the presence of 4.9 grams of the 1,4-butanediol diacetate (13% unconverted), 12.9 grams of tetrahydrofuran (95% yield based on 87% conversion), 29.1 grams of acetic acid, and small quantities of the byproduct diols (2methyl-1,3-propanediol and 1,2-butanediol), and their various acetate derivatives and olefinic decomposition products.

EXAMPLE 7

A miniplant is constructed and operated for the production of tetrahydrofuran from propylene via the disclosed cyclic process. An 8 ft. × 1 in. diameter stainless steel tube is charged with one liter (1000 grams) of catalyst composed of alumina impregnated with palladium (0.3%) and potassium acetate (3%). The reactor temperature is maintained at 180° C. (circulating oil jacket) while a mixture per hour of 2000 grams of propylene, 600 grams of acetic acid, 170 grams of oxygen and 900 grams of water is passed through. The output per hour is a mixture of about 960 grams of allyl acetate and 1050 grams of water, in addition to 18 grams of carbon dioxide and the excess propylene and oxygen, which are recycled. The allyl acetate phase, which contains about 0.1% acetic acid, is separated and used directly in the second stage of the process.

A 2 liter stirred autoclave heated at 125° C. is pressurized with 3000 psi of 2:1 hydrogen/carbon monoxide and charged with a mixture of 400 grams of the allyl acetate, 8.0 grams of cobalt octacarbonyl and 400 ml. of benzene. An exothermic reaction and gas uptake ensue. After 15 minutes at 125°–145° C., the product mixture is pumped from the autoclave, cooled and vented. It is then decobalted by heating at 110° C. for 10 minutes in a closed vessel, the addition of acetic acid being unnecessary because of its presence as a decomposition product. (The cobaltous acetate which forms is filtered off and transformed to cobalt octacarbonyl by subjection to hydrogen/carbon monoxide at elevated temperature and pressure[160° C., 3000 psi]). The benzene solution is concentrated and the products are flash distilled, affording 474 grams (91% yield) of oxo aldehydes containing minor amounts of the butanediol acetate compounds. A glpc analysis indicates the presence of 4-acetoxybutyraldehyde, 3-acetoxy-2-methylpropionaldehyde and 2-acetoxybutyraldehyde in 7 : 1.5 : 1.5 ratio.

The aldehyde mixture is combined in a stirred autoclave with 50 grams of a 13% cobalt on silica catalyst, subjected to 3000 psi of hydrogen and heated for 15 minutes at 190° C. Reduction to the diol derivatives is complete, in essentially quantitative yield.

After removal of the hydrogenation catalyst by filtration, the product mixture is examined by glpc and found to contain 4-acetoxybutanol, 3-acetoxy-2-methylpropanol and 2-acetoxybutanol, in addition to substantial amounts of the corresponding diacetate and diol disproportionation products (including about 140 grams of 1,4-butanediol diacetate.

The acetate product is combined with 100 ml of water; the mixture is passed directly through an 8 ft. × 1 in. diameter tube containing one liter of the catalyst described in Example 1, at 220°–250° C, over a 30 minute period (contact time 3–10 seconds). Distillation of the effluent affords the tetrahydrofuran-water azeotrope (containing, as indicated by glpc analysis, 176 grams of tetrahydrofuran, 61% yield in the conversion from allyl acetate) and 224 grams of acetic acid (92% yield). The small higher boiling component of the effluent contains minor amounts of the byproduct acetates, diols and olefinic decomposition products. No 1,4-butanediol derivatives remain unconverted.

The acetic acid produced in the final step is recycled to the propylene oxidation stage for production of allyl acetate.

The process as described is operated semi-continuously to provide tetrahydrofuran at about one pound per hour.

It should, of course, be apparent to those skilled in the art that changes may be made in the particular embodiments of the invention described which are within the full intended scope of the invention as defined by the appended claims.

What is claimed is:

1. A process for preparing tetrahydrofuran which comprises the steps of:
   a. reacting propylene, oxygen, and a carboxylic acid in the presence of a catalyst comprising a Group VIII noble metal, or its salts, or its oxides or mixtures thereof at a temperature sufficiently high to provide the desired rate of formation of the corresponding allyl carboxylate but below the temperature at which substantial degradation of the allyl carboxylate occurs;
   b. converting the allyl carboxylate under hydroformylation-hydrogenation conditions to a mixture comprising the carboxylic acid mono and di esters of 1,4-butanediol, 1,2-butanediol and 2-methyl-1,3-propanediol;
   c. heating said mixture in the vapor phase at a temperature from about 180° to about 270° C with water in the presence of a hydrolysis-dehydroacyloxylation catalyst selected from the group consisting of zeolites, silica, alumina, silica-aluminas, silica-magnesias and acidic clays to produce tetrahydrofuran and the carboxylic acid; and
   d. isolating the carboxylic acid in a form suitable for recycling to (a).

2. A process for preparing tetrahydrofuran which comprises the steps of:
   a. reacting propylene, oxygen and acetic acid in the presence of a catalyst comprising a Group VIII noble metal, or its salts or its oxides or mixtures thereof, at a temperature sufficiently high to provide the desired rate of formation of allyl acetate but below the temperature at which the substantial degradation of allyl acetate occurs;
   b. converting the allyl acetate under hydroformylation-hydrogenation conditions to a mixture comprising 1,4-butanediol diacetate, 2-methyl-1,3-propanediol diacetate and 1,2-butanediol diacetate, as well as the corresponding monoacetates and diols;
   c. heating said mixture in the vapor phase at a temperature from about 180° to about 270° C with water in the presence of a hydrolysis-dehydroacyloxylation catalyst selected from the group consisting of zeolites, silica, alumina, silica-aluminas, silica-magnesias and acidic clays to produce tetrahydrofuran and acetic acid; and
   d. isolating the acetic acid in a form suitable for recycling to (a).

* * * * *